United States Patent
Tsutsui

(10) Patent No.: US 7,353,823 B2
(45) Date of Patent: Apr. 8, 2008

(54) POWDER CHEMICAL FEEDING DEVICE FOR NASAL CAVITY

(75) Inventor: Tatsuo Tsutsui, 9-8, Nakahara 4-chome, Isogo-ku, Yokohama-shi, Kanagawa (JP) 235-0036

(73) Assignees: Bioactis Limited, Tokyo (JP); Tatsuo Tsutsui, Kanagawa (JP)

( * ) Notice: Subject to any disclaimer, the term of this patent is extended or adjusted under 35 U.S.C. 154(b) by 340 days.

(21) Appl. No.: 10/512,857

(22) PCT Filed: May 13, 2003

(86) PCT No.: PCT/JP03/05924

§ 371 (c)(1),
(2), (4) Date: Jan. 12, 2005

(87) PCT Pub. No.: WO03/095008

PCT Pub. Date: Nov. 20, 2003

(65) Prior Publication Data

US 2005/0177095 A1    Aug. 11, 2005

(30) Foreign Application Priority Data

May 14, 2002 (JP) .............................. 2002-138058

(51) Int. Cl.
*A61M 11/00* (2006.01)
(52) U.S. Cl. ..................... 128/203.21; 128/203.15; 128/203.19
(58) Field of Classification Search .......... 128/203.12, 128/203.15, 203.19, 203.21, 203.22, 203.23, 128/203.24
See application file for complete search history.

(56) References Cited

U.S. PATENT DOCUMENTS 3,888,252 A * 6/1975 Side et al. ............. 128/203.15

(Continued)

FOREIGN PATENT DOCUMENTS

| JP | 59-34267 | 2/1984 |
| JP | 9-253208 | 9/1997 |

(Continued)

OTHER PUBLICATIONS

U.S. Appl. No. 10/550,490, in the name of Tatsuo Tsutsui, filed Mar. 27, 2003.

(Continued)

*Primary Examiner*—Steven O. Douglas
(74) *Attorney, Agent, or Firm*—Greenblum & Bernstein, P.L.C.

(57) ABSTRACT

In a device to deliver a powdery medicine into a nasal cavity, one-way valve 33 is built in an air flow passage 31 of a capsule housing/holding part 30, the one-way valve 33 is controlled for the opening pressure by a spring 34 and opens by a pressure of air from the pump 50, the one-way valve end 71 does not interfere the setting/detaching operation of the capsule setting/detaching part 40 and the capsule K when the one-way valve 33 is opened and intrudes as far as the inside of the capsule to disperse the medicine in the capsule K when the one-way valve 33 is opened by pressing of the pump 50 upon dosing thereby capable of reliably dosing at a adequate dose also including the medicine falling as far as the one-way valve 33 to the nasal cavity of the user.

8 Claims, 8 Drawing Sheets

U.S. PATENT DOCUMENTS

| | | | | | |
|---|---|---|---|---|---|
| 3,906,950 | A | * | 9/1975 | Cocozza | 128/203.15 |
| 3,949,751 | A | * | 4/1976 | Birch et al. | 128/203.15 |
| 5,250,287 | A | * | 10/1993 | Cocozza | 424/45 |
| 5,647,349 | A | * | 7/1997 | Ohki et al. | 128/203.15 |
| 5,810,004 | A | * | 9/1998 | Ohki et al. | 128/203.15 |
| 5,899,202 | A | * | 5/1999 | Ohki et al. | 128/203.22 |
| 5,921,236 | A | * | 7/1999 | Ohki et al. | 128/203.15 |
| 5,989,217 | A | * | 11/1999 | Ohki et al. | 604/94.01 |
| 6,298,846 | B1 | * | 10/2001 | Ohki et al. | 128/203.15 |
| 6,824,080 | B2 | * | 11/2004 | Matsugi et al. | 239/418 |

FOREIGN PATENT DOCUMENTS

| | | |
|---|---|---|
| JP | 2001-95918 | 4/2001 |
| WO | 2004/087243 | 3/2003 |

OTHER PUBLICATIONS

English Language Abstract of JP 5934267.
English Language Abstract of JP 2001-95918.
English Language Abstract of JP 9-253208.

* cited by examiner

POWDER CHEMICAL FEEDING DEVICE FOR NASAL CAVITY

TECHNICAL FIELD

The present invention concerns an optimal device to deliver a powdery medicine into the nasal cavity.

A treatment method to deliver a powdery medicine into the nasal cavity of a patient suffering from asthma or nasal allergy has been known generally. In the treatment method, a powdery medicine filled in a capsule is administered into the nasal cavity using a special delivery device. JP-A No. 59-34267 (hereinafter referred to as prior art) has proposed a delivery device used for the treatment. The device of the prior art comprises a cylindrical member having a pump on the air inlet and a concave part in which a capsule is inserted on the air exit of the cylindrical member. A top end part is fitted into the concave part to form a capsule housing part, and an air guide passage having a valve mechanism is formed from the capsule housing part to the pump.

Another valve mechanism is provided to the other side of the pump, and air is supplied to the capsule housing part through the air guide passage having a valve mechanism upon pressing of the pump, and external air is sucked into the pump through the another valve upon removal of the pump pressure.

Further, the cylindrical member has, at its top end, a cap fitted to the top end and a needle is extended axially in the cap so as to perforate both axial ends of the capsule by engaging the cap in a state of fitting the concave part of the cylindrical member and the top end having an opening.

In the prior art device of the constitution described above, after inserting the capsule filled with a powdery medicine into the concave part of the cylindrical member, the capsule is inserted and fixed in the capsule housing portion by fitting the top end. Then a cap is fitted to the top end made of a hard resin to perforate both axial top ends of the capsule by a needle built inside the cap and guided to the top end.

Then, when the medicine is dosed, a user detaches the cap from the cylindrical member and inserts the top end into one of the nasal nostril and presses the pump. Then, when the pump is pressed, air from the pump flows through the air guide passage into the capsule to deliver the medicine in the capsule to the nasal cavity of the user. Further, by repeating the operations for both nasal cavities, the medicine is dosed to both of the nasal cavities.

In the device of the prior art described above, while the capsule is perforated by a needle built in the detachable cap and then the pump is pressed to deliver and dose the medicine in the capsule to the user's nasal cavity. However, in a case of a medicine with poor flowability or separability or a medicine tending to deposit in the inner surface of the capsule due to static charges generated to the capsule, the medicine would remain in the capsule even after the frequent pump actuation, to result in a problem failing to deliver at an adequate dose for a user.

The subject of the present invention is to provide a device to deliver a powdery medicine into the nasal cavity capable of overcoming such a problem.

DISCLOSURE OF THE INVENTION

A device to deliver a powdery medicine into the nasal cavity according to the present invention provided for solving the subject described above comprises a capsule housing/holding part for housing and holding a capsule filled with a powdery medicine, a pump installed in the capsule housing/holding part for supplying dosing air to the capsule housing/holding part, a medicine delivery part installed in the capsule housing/holding part for delivering and dosing the medicine in the capsule from the pump to the nasal cavity of a user, and a one-way valve built in the air flow passage an opening pressure of which is controlled by a spring for separating and dispersing the medicine in the capsule by the airflow rectification in the capsule resulting from the entrance of one end thereof on the capsule side into the capsule upon the pump actuation.

That is, the device to deliver powdery medicine into nasal cavity according to the present invention comprises a one-way valve as a movable member for separating and dispersing a medicine in a capsule which is actuated upon medicine spraying to the capsule housing/holding part and such a one-way valve can completely prevent falling and backward flowing of the medicine after perforation from falling and backwardly flowing into the pump and can deliver and dose a prescribed amount of the medicine filled in the capsule reliably to the nasal cavity of the user.

Figure 1:
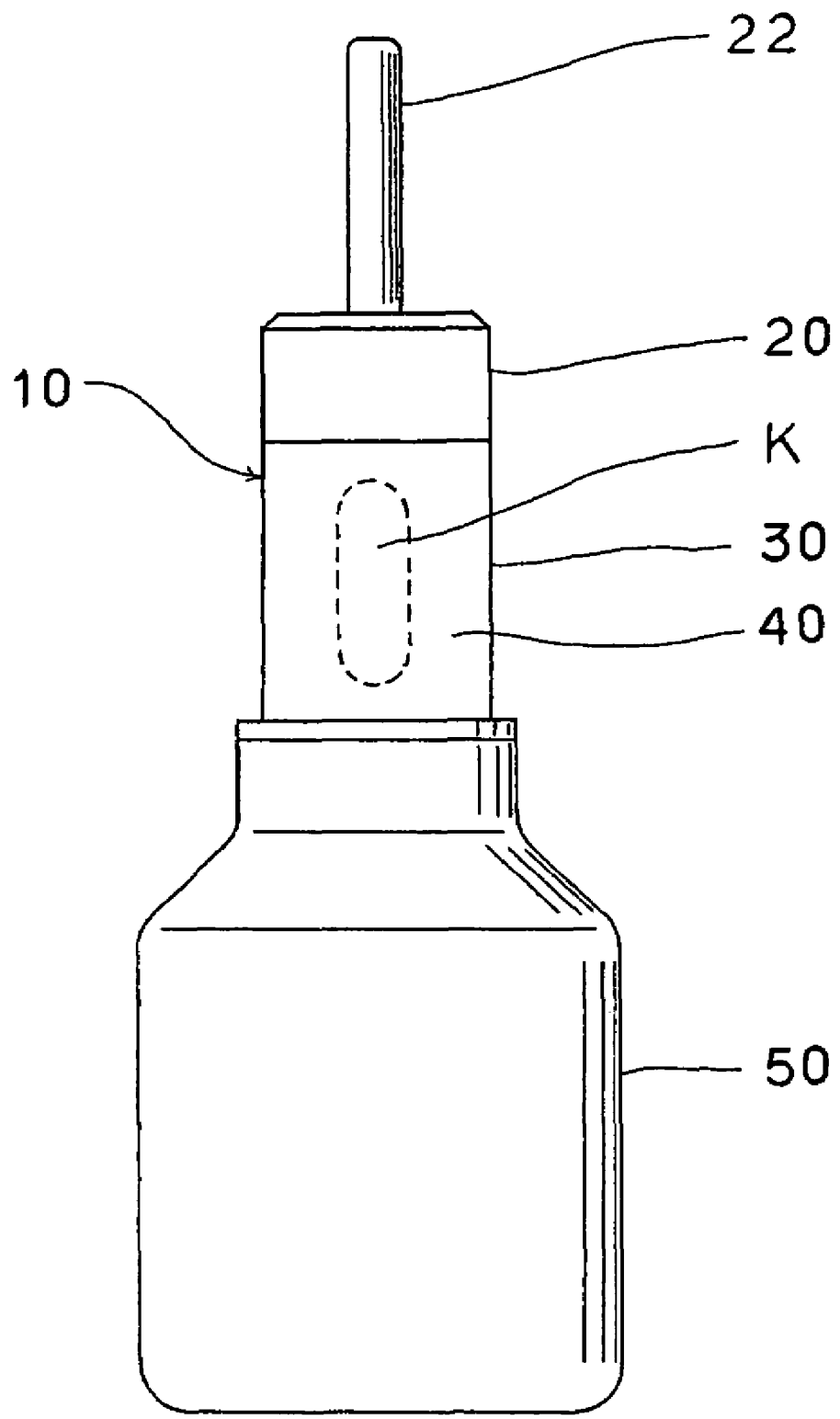
FIG. 1 is a side elevational view illustrating an embodiment of a powdery medicine delivery device according to the present invention.

Each of the references has the following meanings
10 device to deliver powdery medicine into nasal cavity
20 medicine delivery part
21 medicine passage
22 nozzle
30 capsule housing/holding part
31 air flow passage
33 one-way valve
34 spring
35 air flow inlet
36 abutment surface
37 protrusion
38 lower portion of the capsule housing/holding part
40 capsule setting/detaching part
41 capsule attaching/detaching concave part
42A, 42B capsule cut end discharge part
44 drawing end
45 protrusion for setting/detaching part
46 end face for capsule setting/detaching part
50 pump
51 attaching part 52 bottom
53 pressing part
54 air intake valve
55 air intake valve
56 intake valve body
60A, 60B cutting blade
71 one-way valve end
72 flow control surface
73 reduced diameter valve portion
K capsule
KA, KB capsule end

DETAILED DESCRIPTION

The present invention is to be described specifically by way of embodiments with reference to the drawings. An embodiment of the present invention is shown in FIG. 1 to FIG. 8.

Figure 2:
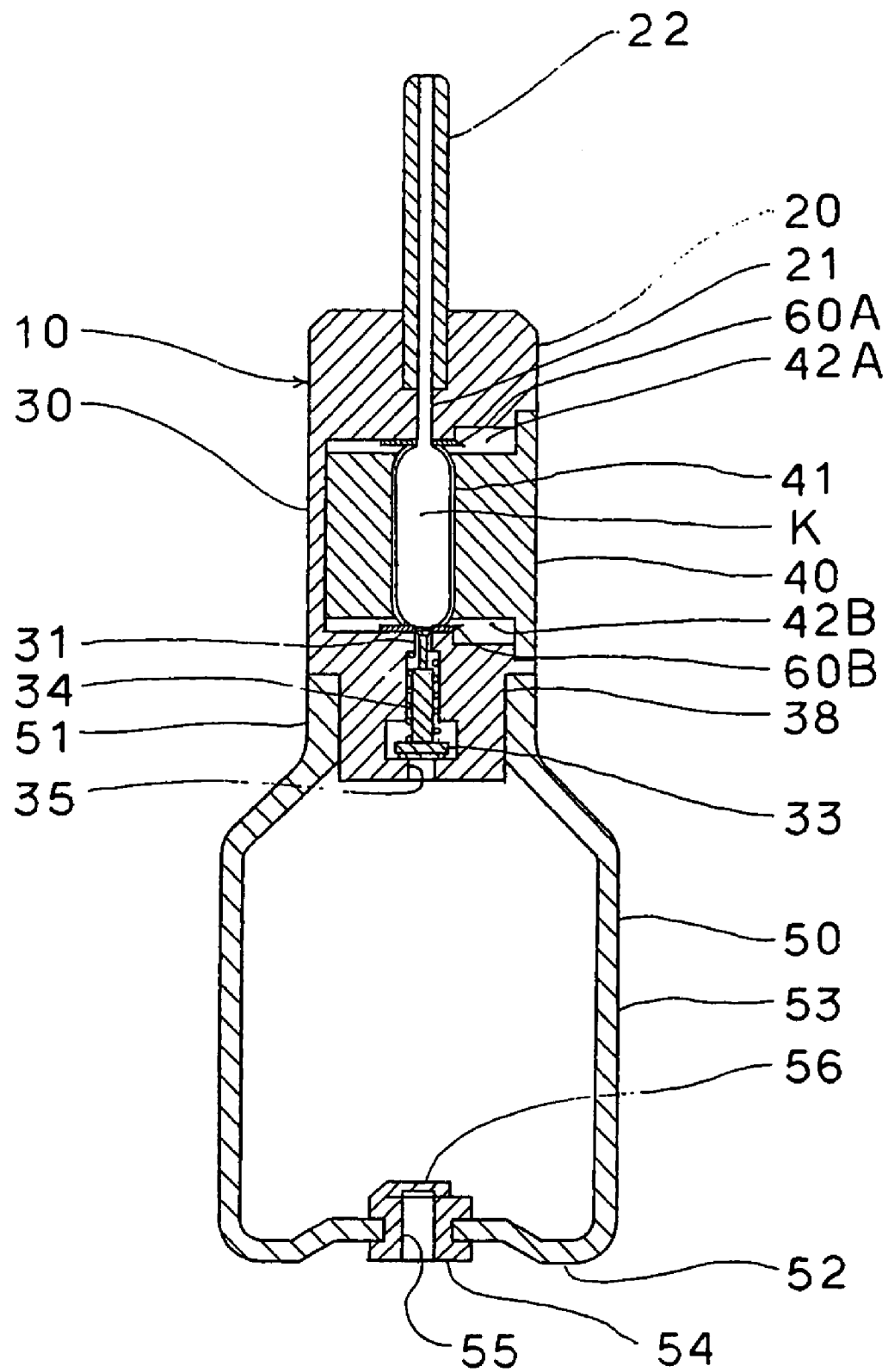
FIG. 2 is a cross sectional view illustrating an embodiment of a powdery medicine delivery device according to the present invention.
Figure 3:
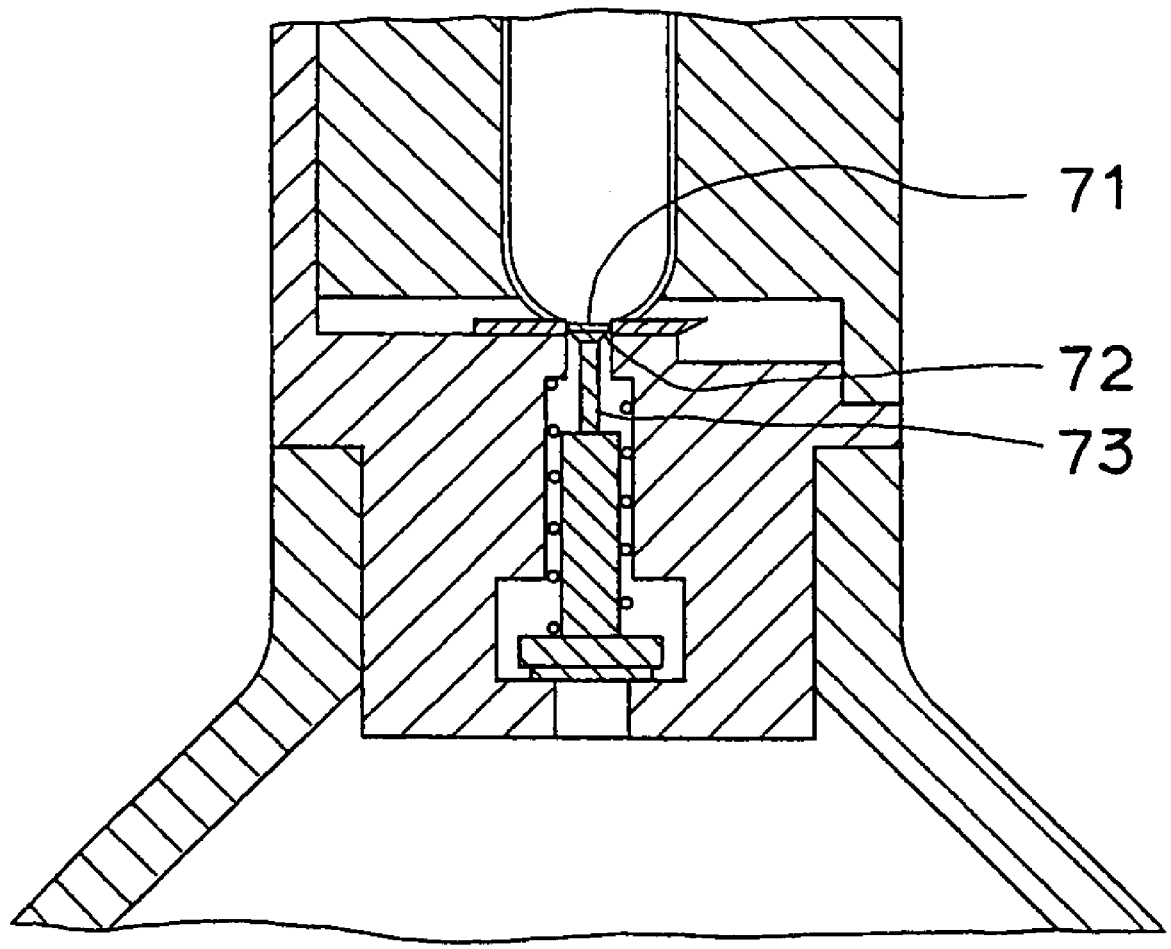
FIG. 3 is a detailed view for a portion of FIG. 2.

FIG. 1 is a side elevational view of an embodiment of a device to deliver a powdery medicine into the nasal cavity according to the present invention, FIG. 2 is a cross sectional side elevational view of a device to deliver a powdery medicine into the nasal cavity shown in the embodiment, and FIG. 3 is a detailed view for FIG. 2.

In the drawings, a device 10 to deliver a powdery medicine into the nasal cavity comprises, generally, a capsule housing/holding part 30 for housing and holding a capsule K together with a medicine delivery part 20, a capsule setting/detaching part 40 built drawably in the capsule housing/holding part 40 and a pump 50 installed in the air inlet side of the capsule housing/holding part 30 for supplying air to the capsule, and cutting blades 60a, 60b situated at both axial ends of the capsule K of the capsule setting/detaching part 40 of the capsule housing/holding part 33 for perforating both axial ends of the capsule K by setting/detaching operation of the capsule setting/detaching part 40.

In the medicine delivery part 20 of this embodiment, a medicine passage 21 is built in an upper part (air exit side) with respect to the axial direction of the capsule K of the capsule housing/holding part 30, and a nozzle 22 made of a flexible tube is formed to the top end of the medicine passage 21.

In an air flow passage 31 of the capsule housing/holding part 30 axially below the capsule K (air inlet side), a one-way valve 30 is built to prevent falling and backward flowing of the powdery medicine from the capsule K to the pump 50. The one-way valve 33 is adapted to prevent back flow of air such that it opens when the pressure of air from the pump 50 reaches at or higher than a prescribed pressure and closes the air flow inlet 35 when the pressure of air from the pump 50 is lower than the prescribed pressure.

Further, the one-way valve end 71 as the end of the one-way valve 33 on the side of the capsule K is below the surface where the cutting blade 60B is in contact with the capsule K (on the side of the pump 50) when the one-way valve 33 is opened and does not interfere the setting/detaching operation of the capsule setting/detaching part 40 and the capsule K, whereas it intrudes as far as the inside of the capsule K when the pump 50 is pressed and the one-way valve 33 is opened upon dosage to be described later.

The capsule setting/detaching part 40 has a capsule attaching/detaching recess 41 at a position of attaching or detaching the capsule K, such that it can be set and detached drawably in the lateral direction with respect to the axial direction of the capsule K to the capsule housing/holding part 30 and a drawing end 44 of the capsule setting/detaching part 40 is regulated by the abutment of the detaching end 44 to the protrusion 37 built in the capsule housing/holding part 30.

Further, when the capsule setting/detaching part 40 is pushed into the capsule housing/holding part 30, the inlet end is regulated by the abutment of a setting/detaching protrusion 45 of the capsule setting/detaching part 40 against the abutment face 36 of the capsule housing/holding part 30.

The pump 50 is formed from a resilient rubber material into a bottomed cylindrical shape having an attaching part 51, a bottom 52 and a pressing part 53 at the circumferential surface. The attaching part 51 is mounted sealingly to the cylindrical outer circumferential surface of the capsule housing/holding lower part 38 of the capsule housing/holding part 30, and an air inlet valve 54 is attached to a central portion of the bottom 52.

The air intake valve 54 produced using a resilient rubber material and comprises an air inlet form 55 and an inlet valve body 56. The valve is closed when the pump 50 is pressed, while the valve is opened upon restoration of the pump 50 after pressing to supply external air to the pump 50.

The device to deliver a powdery medicine into the nasal cavity according to this embodiment has been constituted as described above. Then, description is to be made to an operation upon perforation of the capsule with reference to FIG. 4 to FIG. 6.

Figure 4:
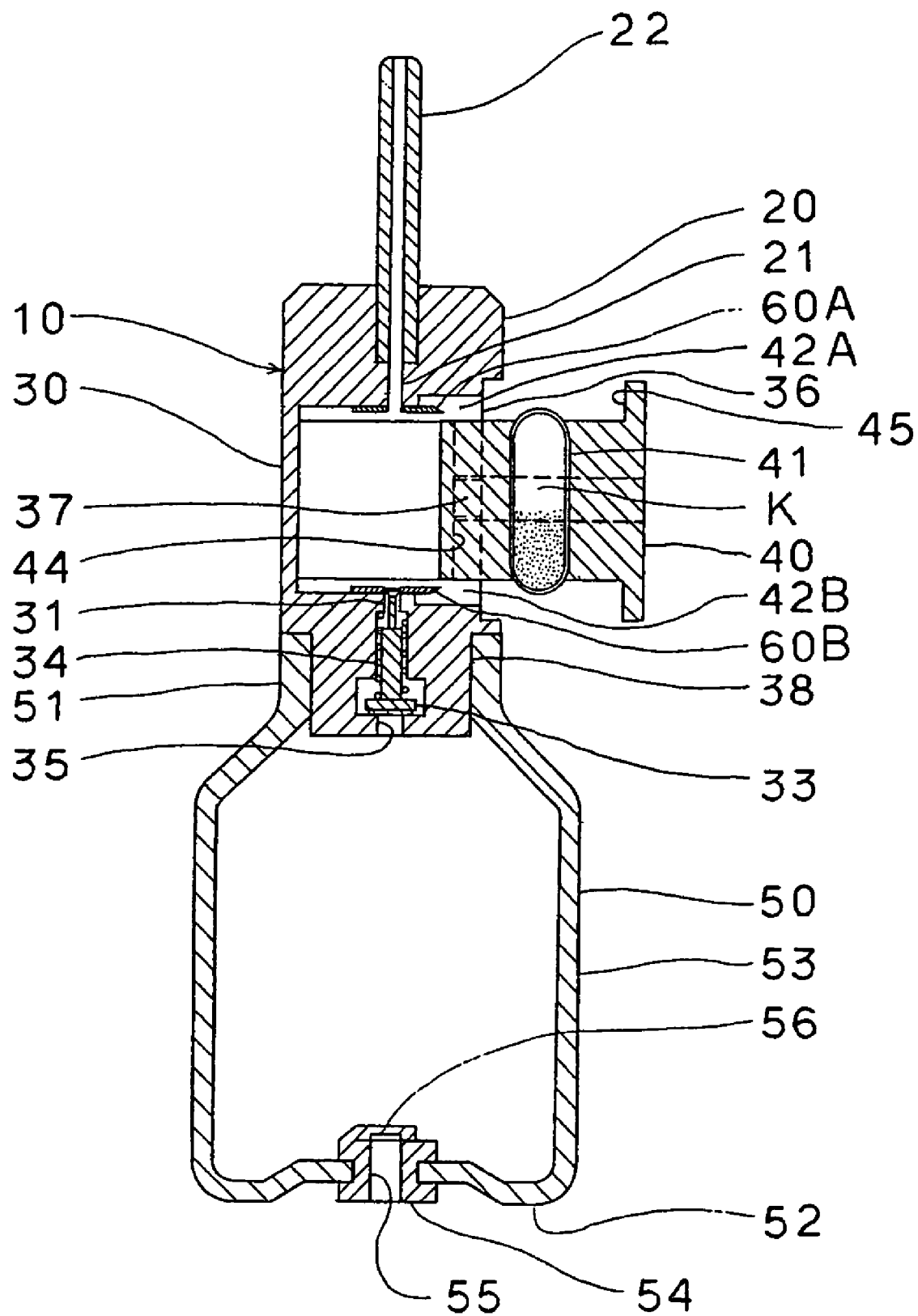
FIG. 4 is a view showing a state of drawing out a capsule setting/detaching part and placing a capsule therein in the embodiment described above.

At first, as shown in FIG. 4, the capsule K is placed in the capsule attaching/detaching concave 41 of the capsule setting/detaching part 40 and the capsule setting/attaching end face 46 of the capsule setting/detaching part 40 is pressed so as to intrude the capsule setting/detaching part 40 into the capsule housing/holding part 30.

Figure 5:
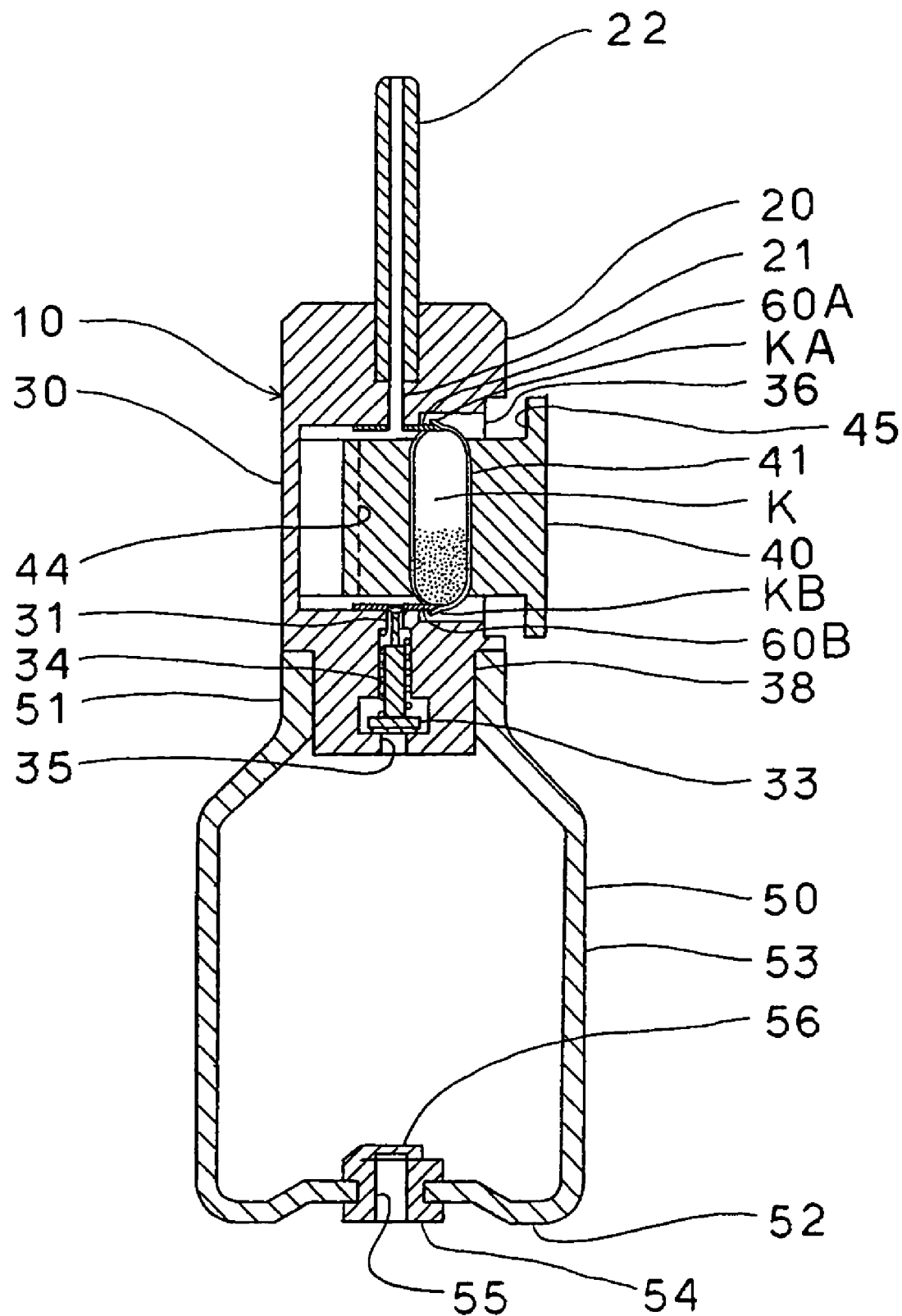
FIG. 5 is a cross sectional view showing a state in which cutting blades are cutting capsule ends in the course where the capsule setting/detaching part with the capsule placed therein is inserted into the capsule housing/holding part.

Then, as shown in FIG. 5, as the capsule K placed in the capsule setting/detaching concave 41 of the capsule setting/detaching part 40 intrudes into the capsule housing/holding part 30, the cutting blades 60A, 60B built laterally at both axial ends of the capsule K in the capsule housing/holding part 30 cut off both axial ends KA, KB of the capsule K, thereby perforating both ends of the capsule K.

Further, when the capsule setting/detaching end face 46 of the capsule setting/detaching part 40 is pushed to abut the setting/detaching protrusion 45 against the abutment surface 36 of the capsule housing/holding part 30, the capsule K that was already perforated both axial ends pass completely through to the medicine passage 21 of the medicine delivery part 20 and the air flow passage 31 of the capsule housing/holding part 30 to be in a state ready for dosing the medicine.

Figure 6:
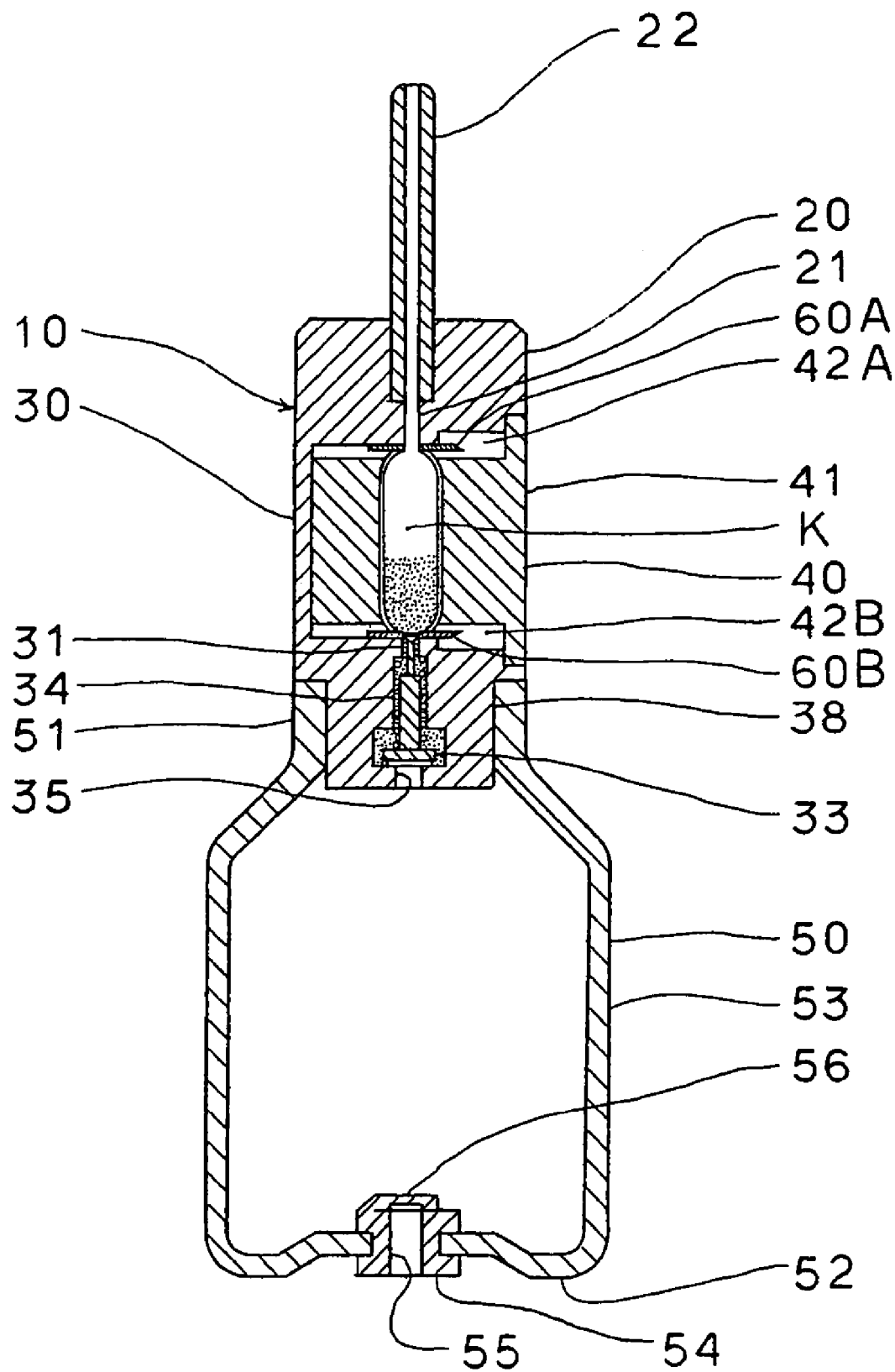
FIG. 6 is a cross sectional view showing a state in which the capsule ends are cut off by cutting blades, and the medicine in the capsule upon completion of perforation is falling and flowing backwardly to the pump in the embodiment described above.

In this case, as shown in FIG. 6, the medicine in the capsule K perforated both axial ends thereof falls toward to the airflow passage 31. Since the one-way valve 33 is closed by the function of the spring 34, the medicine is prevented from falling and flowing backwardly to the pump 50.

As described above, upon perforation in the device 10 to deliver a powdery medicine into the nasal cavity in this embodiment, holes are easily perforated at both axial ends of the capsule K only by the operation of housing the capsule K in the device 10 to deliver a powdery medicine into the nasal cavity and falling and backward flowing of the medicine to the pump after perforation is completely prevented by the one-way valve 33.

Then, operation upon dosing the medicine to the user after perforation of the capsule K is to be described with reference to FIG. 7 and FIG. 8 as detailed views for the portion thereof.

Figure 7:
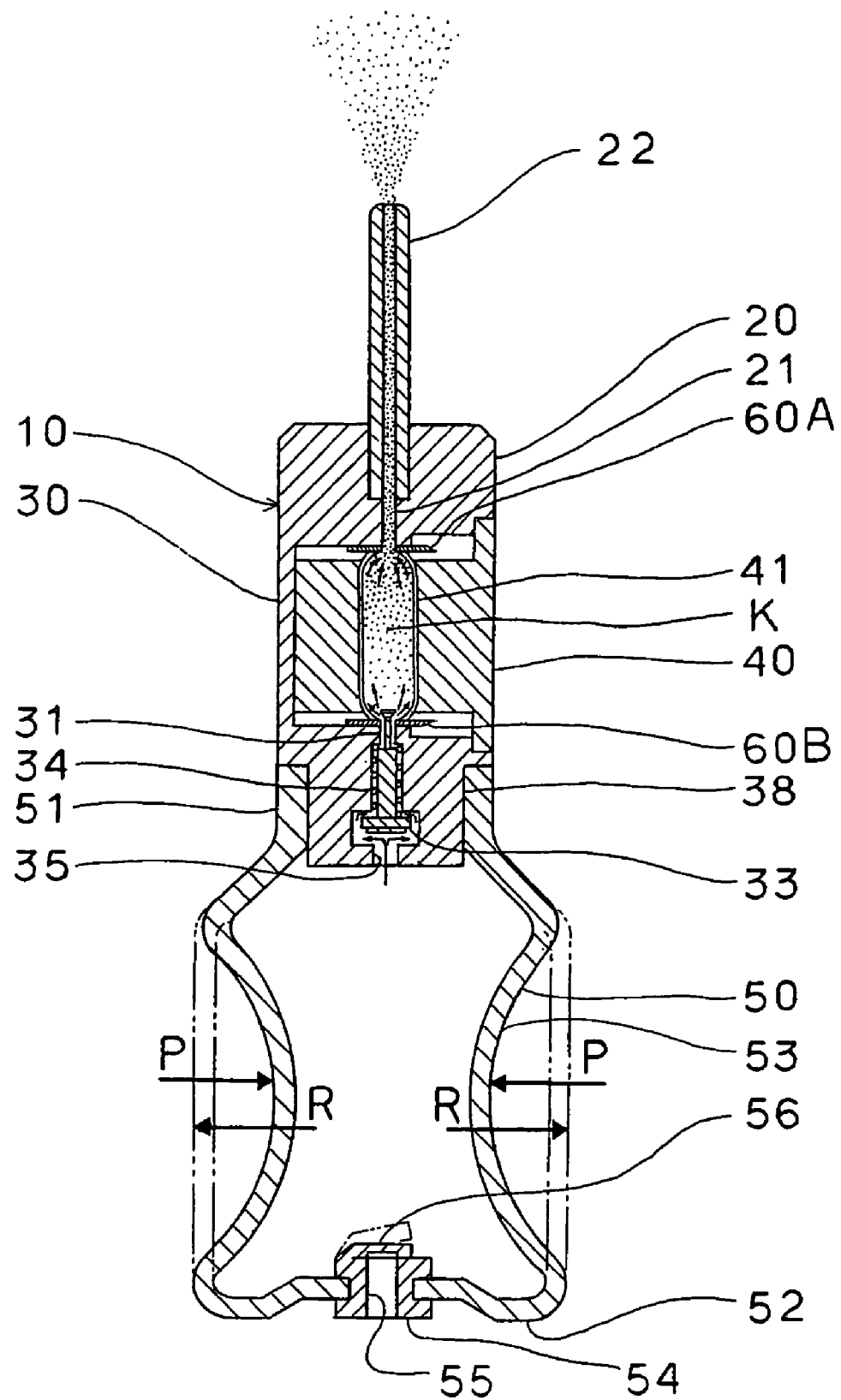
FIG. 7 is a cross sectional view in a state where the medicine in the capsule is under delivery and dosing by pressing the pump in the embodiment described above.
Figure 8:
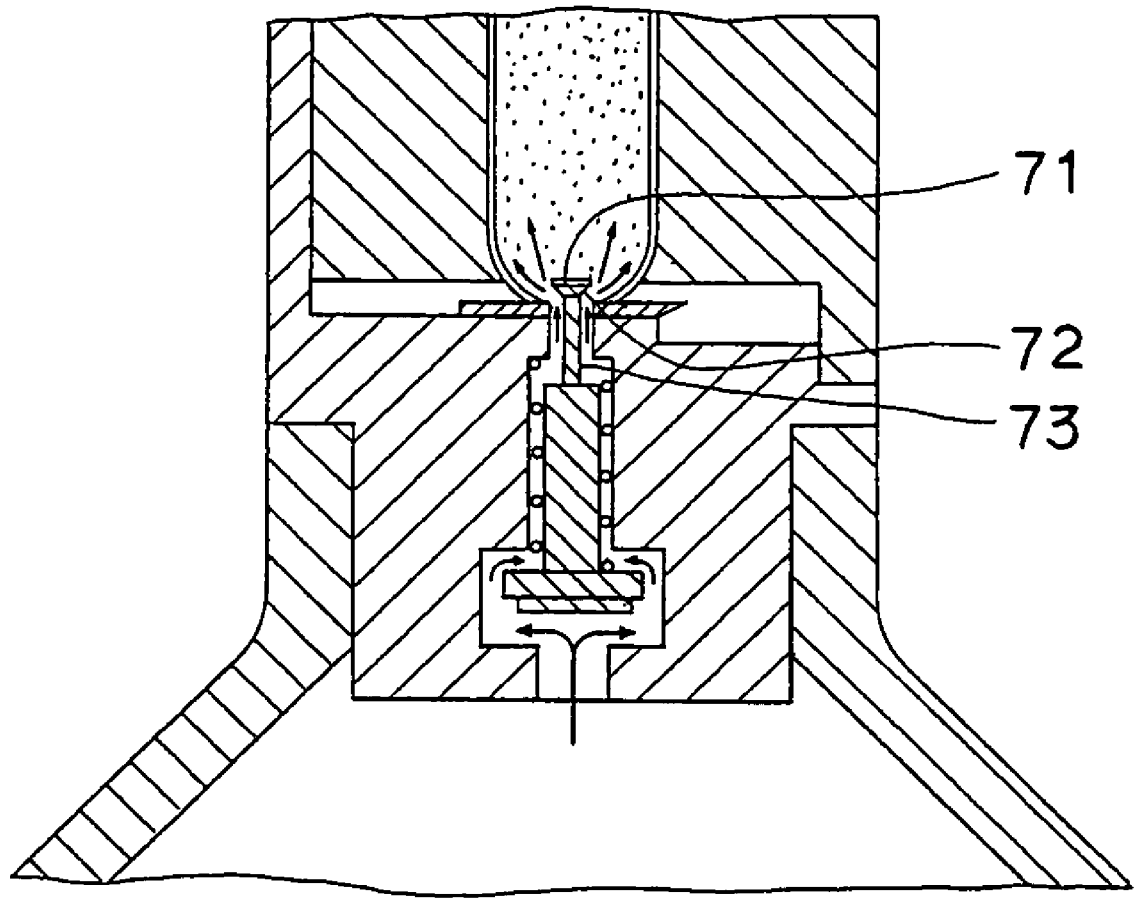
FIG. 8 is a detailed for a portion of FIG. 7.

At first, when the nozzle 22 of the medicine delivery part 20 is inserted into the nasal nostril of a user and the pressing part 53 of the pump 50 is pressed in the direction of an arrow P as shown in FIG. 7, the pressure of air loaded on the one-way valve 33 increases and, when it reaches to a predetermined pressure, the one-way valve 33 is opened in which air is supplied from the pump 50 through the one-way valve 33 and the air flow passage 31 to the capsule K.

Thus, air from the pump 50 flows from the inside of the capsule K by way of the medicine passage 21 and the nozzle 22 to the nasal cavity of the user.

In this process, the one-way valve end 71 is at a position detaching from the air flow passage 31 and entering in the capsule K and, since the valve reduced diameter part 72 is within the air flow passage 31, it does not hinder the air flow.

A portion of air passing the air flow passage 31 hits on the flow control surface 72 succeeding to the valve reduced diameter part 73 to generate an air flow along the inner surface of the capsule K and an air flow agitating the inside of the capsule K thereby separating and dispersing the medicine coagulated in the capsule K or deposited to the inner surface of the capsule K, which is delivered and dosed to the user's nasal cavity together with other air and medicine.

Further, the medicine that dropped and flowed backwardly upon perforation as far as the one-way valve 33 is sent by air from the pump 50, and delivered and dosed together with the medicine in the capsule K to the nasal cavity of the user. As a result, a prescribed amount of the medicine filled in the capsule K can be reliably delivered and dosed to the user's nasal cavity.

Further, just before completion of pressing to the pump 50, pressure of air loaded on the one-way valve 33 is weakened and when it becomes lower than a predetermined pressure to open the one-way valve 33, the one-way valve is closed. Just before the closure of the one-way valve 33, air still flows from the pump 50 to the capsule K. Accordingly, the medicine in the capsule K and the air flow passage 31 does not fall and flow backwardly to the pump 50 and falling and backward flow of the medicine to the pump 50 can be prevented reliably.

Further, when the pressing to the pump 50 is completed and the pressure is removed, the pressing part 53 of the pump 50 having the rubber resiliency restores in the direction shown by an arrow R to cause a negative pressure in the pump 50, so that the intake valve body 56 of the air intake valve 54 is opened by the pressure of the external air and air flows into the pump 50 from the outside by way of the air intake hole 55 to restore the pressing portion of the pump 50 to an original state as shown by dotted chains.

In the device 10 to deliver a powdery medicine into the nasal cavity of this embodiment, the capsule housing/holding part 30 comprises the one-way valve 33 for preventing falling and backward flowing of the powdery medicine falling and flowing backwardly from the capsule K to the pump 50. The one-way valve 33 is adapted such that it opens when the pressure of air from the pump 50 reaches a predetermined pressure, where the one-way valve end 71 detaches from the air flow channel 31 and enters in the capsule, and the valve reduced diameter part 73 is within the air flow passage 31, so that it does not hinder the air flow. Then, air passing through the air flow passage 31 hits on the flow control surface 72 succeeding to the valve reduced diameter part 73 to generate an air flow along the inner surface of the capsule K or an air flow agitating the inside of the capsule K. Accordingly, even in the case of using a medicine with poor flowability or separability or a medicine tending to deposit on the inner surface of the capsule K due to static charges generated in the capsule K, the medicine coagulated in the capsule K or the medicine deposited in the surface of the capsule K is separated and dispersed and a medicine of a prescribed amount filled in the capsule K can reliably be delivered and dosed also including the medicine fallen and flown backwardly as far as the one-way valve together with air to the nasal cavity of the user thereby capable of dissolving the problems in the prior art.

INDUSTRIAL APPLICABILITY

As has been described above, according to the present invention, since the one-way valve end part is equipped with the end of the one-way valve on the side of the capsule the opening pressure of which is controlled by the spring between the capsule housing/holding part and the pump for preventing falling and backward flow of the medicine falling and flowing backwardly from the capsule after perforation from falling and flowing backwardly to the pump and dosing such medicine together with the medicine in the capsule by the pump actuation, when the one-way valve is opened by air from the pump upon administration, air passing through the air flow passage abuts against the flow control surface of the one-way valve succeeding to the valve reduced diameter part to generate an air flow along the inner surface of the capsule and an air agitating the inside of the capsule to separate and disperse the medicine deposited to the inner surface of the capsule or the medicine coagulated in the capsule and they can be delivered and dosed to the nasal cavity of the user including the thus separated and dispersed medicine falling and flowing backwardly as far as the one-way valve together with air.

Accordingly, the present invention can provide advantageous effects capable of resolving the problem for the occurrence of residues of medicine in the capsule in a case of using a medicine with poor flowability or separability or a medicine tending to deposit to the inner surface of the capsule due to static charges generated in the capsule, which was difficult to be solved in the prior art, and capable of reliably delivering and dosing a prescribed amount of the medicine filled in the capsule to the nasal cavity of the user.

The invention claimed is:

1. A device for delivering a powdery medicine into the nasal cavity comprising:
    a capsule housing and holding portion configured to house and hold a capsule filled with a powdery medicine;
    a pump configured to supply dosing air by way of an air flow passage formed in the capsule housing and holding portion; and
    a medicine delivery portion configured to deliver and dose medicine in the capsule to a nasal cavity of the user by air supplied from the pump;
wherein the capsule housing and holding portion comprises cutting blades that remove both axial ends of the capsule so as to form an air flow passage extending from the pump through the inside of the capsule to the medicine delivery portion, the air flow passage comprising a one-way valve configured to prevent backward flow from the capsule to the pump, the one-way valve having a flow control surface formed at an end of the valve configured to enter the inside of the capsule, upon valve opening, for forming a flow-control surface where a portion of air passing through the air flow passage contacts the surface to generate an air flow along an inner surface of the capsule.

2. The device for delivering a powdery medicine according to claim 1, further comprising a capsule setting and detaching portion configured to move relative to the capsule housing and holding portion and wherein the cutting blades are configured to cut off both ends of the capsule when the capsule setting and detaching portion is moved into the capsule holding and housing portion.

3. The device for delivering a powdery medicine according to claim 1, wherein the flow control surface is configured so that the air flow generated along the inner surface of the capsule is sufficient to separate and disperse medicine coagulated in the capsule or deposited on the inner surface of the capsule.

4. The device for delivering a powdery medicine according to claim 1, wherein the one way valve is configured so that medicine that falls thereon, after removal of the ends of capsule, is retained and air supplied from the pump delivers the retained medicine to the nasal cavity.

5. A device for delivering a powdery medicine into the nasal cavity comprising:
   a capsule housing and holding portion configured to house and hold a capsule filled with a powdery medicine;
   a pump configured to supply dosing air by way of an air flow passage formed in the capsule housing and holding portion;
   a medicine delivery portion configured to deliver and dose medicine in the capsule to a nasal cavity of the user by air supplied from the pump; and
   a capsule setting and detaching portion configured to move relative to the capsule housing and holding portion in a reciprocating motion, from a first position in which the capsule may be placed in the capsule setting and detaching portion to a second position within the capsule housing and holding portion;
wherein the capsule housing and holding portion comprises cutting blades that remove both axial ends of the capsule so as to form an air flow passage extending from the pump through the inside of the capsule to the medicine delivery portion, the air flow passage comprising a one-way valve configured to prevent backward flow from the capsule to the pump, the one-way valve having a flow control surface formed at an end of the valve configured to enter the inside of the capsule, upon valve opening, for forming a flow-control surface where a portion of air passing through the air flow passage contacts the surface to generate an air flow along an inner surface of the capsule.

6. The device for delivering a powdery medicine according to claim 5, wherein the cutting blades are configured to cut off both ends of the capsule when the capsule setting and detaching portion is moved into the capsule holding and housing portion.

7. The device for delivering a powdery medicine according to claim 5, wherein the flow control surface is configured so that the air flow generated along the inner surface of the capsule is sufficient to separate and disperse medicine coagulated in the capsule or deposited on the inner surface of the capsule.

8. The device for delivering a powdery medicine according to claim 5, wherein the one way valve is configured so that medicine that falls thereon, after removal of the ends of capsule, is retained and air supplied from the pump delivers the retained medicine to the nasal cavity.

* * * * *